United States Patent [19]

Wallshein

[11] 4,130,921
[45] Dec. 26, 1978

[54] METHOD OF MAKING ORTHODONTIC APPLIANCE HAVING REPLACEABLE TOOTH ENGAGING MEANS

[76] Inventor: Melvin Wallshein, 8645 Bay Pkwy., Brooklyn, N.Y. 11214

[21] Appl. No.: 852,148

[22] Filed: Nov. 16, 1977

Related U.S. Application Data

[60] Division of Ser. No. 816,138, Jul. 15, 1977, Pat. No. 4,091,540, which is a continuation-in-part of Ser. No. 708,305, Jul. 26, 1976, Pat. No. 4,054,996.

[51] Int. Cl.² .................... B21F 43/00; B23P 13/00
[52] U.S. Cl. ............................... 29/160.6; 29/423
[58] Field of Search ................... 29/160.6, 423, 424; 32/14 A, 14 E

[56] References Cited

U.S. PATENT DOCUMENTS

| 2,196,516 | 4/1940 | Atkinson | 29/160.6 X |
| 2,266,860 | 12/1941 | Griesinger | 32/14 E |
| 3,525,153 | 8/1970 | Gerber | 32/14 E |
| 3,529,353 | 9/1970 | Schiaroli | 32/14 A |
| 3,893,819 | 7/1975 | Schaiewitz | 29/160.6 |
| 4,077,115 | 3/1978 | Kádár | 29/423 X |

Primary Examiner—Victor A. DiPalma
Attorney, Agent, or Firm—Flynn & Frishauf

[57] ABSTRACT

An orthodontic appliance, such as a plate, has means defining at least one opening therein, and an elongated wire-type member is provided having at least one end which is removably insertable in the opening of the first member. The elongated member has engaging means at an end thereof which resiliently deforms to lockingly and non-rotatably engage an inner surface portion of the opening which has means for releasably engaging the engaging means of the elongated member.

4 Claims, 11 Drawing Figures

METHOD OF MAKING ORTHODONTIC APPLIANCE HAVING REPLACEABLE TOOTH ENGAGING MEANS

This is a division of application Ser. No. 816,138, now U.S. Pat. No. 4,091,540, filed July 15, 1977, which in turn is a continuation-in-part of application Ser. No. 708,305, now U.S. Pat. No. 4,054,996, filed July 26, 1976.

The present invention relates to orthodontic appliances, and more particularly to orthodontic appliances having an elongated wire-type member which is removably insertable in an opening of an orthodontic appliance, such as a removable plate.

The invention is still more particularly applicable to removable dental plates having wire-type members protruding therefrom for performing either a holding function in the mouth or an orthodontic tooth moving function. In such othodontic appliances, the wire-type elongated members protruding therefrom often break off, especially at around the point at which they extend out from the appliance, such as a plate. Heretofore, in order to repair such a plate, it has been necessary to remove the plate from the wearer's mouth, take a new set of impressions, have the plate repaired, and then reinstall the plate at a subsequent visit. This is a highly time-consuming operation and creates patient discomfort and inconvenience, as well as being expensive to the patient due to the fact that two visits to the orthodontist, or the like, are required to effect a repair.

It is the object of the present invention to provide an orthodontic device having a removable elongated wire-type member inserted therein, the wire-type member being removably and lockingly engaged in the appliance so as to be non-rotatable in the appliance after it is locked therein.

A further object of the present invention is to provide such an appliance which is particularly suitable for orthodontic use and wherein the elongated wire-type member is quickly and easily removable from the appliance so as to be easily replaced in a quick and inexpensive manner.

A still further object of the present invention is to provide such a device which is easily fabricated and which is particularly suitable to mass production techniques.

SUMMARY OF THE INVENTION

According to the present invention, an orthodontic appliance comprises a first member adapted to be located in a mouth and in proximity to a tooth, the first member having means defining at least one opening therein, the opening having at least one depression in an inner surface thereof; and an elongated wire-type member having at least one end removably insertable in the at least one opening of the first member, and further including means for cooperatively coupling same to at least one tooth. The at least one end of the elongated member has a main portion and a bent back portion, at least a portion of the one end of the elongated member being resilient in a direction substantially perpendicular to the length of the elongated member, at least one of the main portion and bent back portion having a contoured releasable cooperative engaging means for releasably engaging the at least one depression in the inner surface of the opening for lockingly and non-rotatably engaging the elongated wire-type member in the opening, whereby upon application of a removal force greater than the locking force, the elongated wire-type member may be removed from the at least one opening to permit insertion of another elongated wire-type member therein.

A method of making an orthodontic appliance according to the present invention comprises forming an elongated member with a main portion and a bent back portion thereon, the main and bent back portions being spaced from each other; forming undulations on a surface of at least one of the main and bent back portions, the main and bent back portions being spaced from each other; filling the space between the main and bent back portions with a filler material which is later removable; molding a member around the main and bent back portions with the filler material therebetween so that the molded member may have an inner surface substantially conforming to the outer surface configuration of the main and bent back portions; and then removing the filler material from the space between the main and bent back portions to permit the main and bent back portions to be resiliently deformed toward each other.

According to a further aspect of the present invention, the elongated member need not have a bent back portion. The elongated member may have, at its end, a bent or deformed portion which is resilient in a direction substantially perpendicular to the length thereof which cooperatively engages at least one depression in the inner surface of the opening of the first member for lockingly and non-rotatably engaging the elongated wire member in the opening. Upon application of a removal force greater than the locking force, the elongated wire-type member may be easily removed from the opening to permit insertion of another elongated wire-type member therein

DETAILED DESCRIPTION

Figure 1:
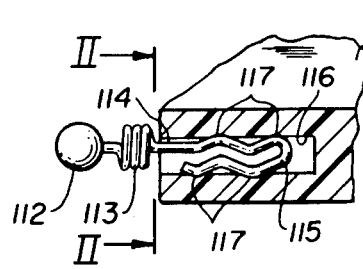
FIG. 1 illustrates an embodiment of the present invention in part sectional form.
Figure 2:
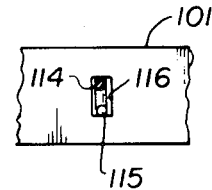
FIG. 2 is a cross-section taken along the line II—II in FIG. 1.

FIG. 1 illustrates an embodiment of the present invention comprising a first member 101 which may be part of, for example, the plate 1 shown in FIGS. 1 and 2 of my prior U.S. Application Ser. No. 708,305. In the present embodiment, the first member 101 is preferably made of a substantially rigid, non-resilient material.

As shown in FIG. 1, the orthodontic device of the present invention comprises an elongated member 114 having a ball clasp 112 attached thereto via a coil spring portion 113. The elongated member 114 has a bent back portion 115 which is resiliently sprung away from the main portion 114. The end of the elongated member 114 and the bent back portion 115 have undulations or a zigzag surface configuration. The plate member 101 has depressions 117 formed in the inner surface of an opening 116 therein. When the elongated member is inserted into the opening 116, the resiliency of the end portion of the elongated member and the bent back portion 115 will cause the end portion of the elongated member to resiliently deform so as to be insertable into the opening 116 and to spring against the depressions 117 in the opening 116 so as to firmly and securely lock the elongated member in engagement with the plate 101. The elongated member may be easily removed from the plate 101 by pulling same outwardly of the whole against the resilient forces in the end of the elongated member and in the bent over portion.

In order to prevent rotation of the elongated member in the opening 116, the opening 116 may be made generally rectangular, as shown in FIG. 2, or oval (not shown).

Figure 3:
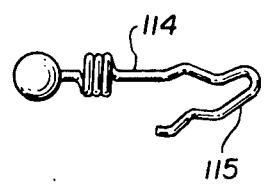
FIG. 3 illustrates a modification to the device of FIG. 1.

In order to enhance the engagement force of the elongated member in the opening 116, the bent back portion 115 may be sprung away from the main portion of the elongated member 114 as shown in FIG. 3. During insertion, the bent back portion 115 is resiliently moved toward the main portion 114 of the elongated member, the bent back portion being biassed away from said main portion so that retention in the opening 116 is enhanced.

It is often desirable to manufacture the plate 101 by molding same around the members to be inserted therein. However, ordinary techniques are impractical in the case of the device of FIGS. 1-3 since the molded material will tend to fill the space between the bent back portion 115 and the main portion 114 of the elongated member. In order to obviate this disadvantage, the space between the elongated member 114 and the bent back portion 115 may be filled with, for example, a material such as wax, during the molding process so as to keep the space free of molded material. After the molding operation is completed, the wax may be removed, for example by melting same out, thereby opening the space between the main portion of the elongated member and the bent back portion 115. This then permits the bent back portion to resiliently move toward the main portion of the elongated member for easy removal and insertion into the plate 101.

Figure 5:
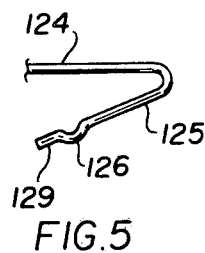
FIGS. 5 and 6 illustrate a modified form of the invention.
Figure 6:
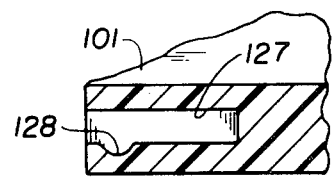

FIG. 5 and FIG. 6 illustrate a modified form of the invention wherein the elongated member 124 has a bent back portion 125 having a bent protrusion 126 formed therein. The corresponding opening 127 of a plate 101 has a depression 128 which engages the bulged out or bent out portion 126. The bent back portion 125 preferably has an extending tip member 129 extending forwardly of the bent out portion 126 for grasping by the operator to move the portion 125 toward the main portion 126 to facilitate removal and insertion of the elongated member out of and into, respectively, the opening 127 in the plate 101. Due to the large angle between the bent back portion 125 and the main portion 124 of the elongated member, a high degree of retention force is obtained by virtue of the resiliency of the material from which the elongated member is made.

Figure 7:
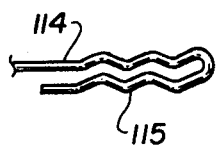
FIGS. 7 and 8 illustrate side and top views, respectively, of a modification of the embodiment of FIG. 1.
Figure 8:
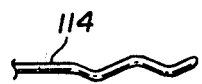

FIG. 7 illustrates a further embodiment of the invention, similar to that of FIG. 1, except that the elongated member and bent back portion 115 are further undulated in a plane perpendicular to the plane of undulation shown in FIG. 7. FIG. 8 is a top view of the embodiment of FIG. 7 and shows such additional undulations.

In the instance of FIGS. 7 and 8, the opening 116 is formed with depressions, such as depressions 117, on the side or vertical running walls thereof as shown in FIG. 2 to further enhance engagement of the elongated member in the opening 116.

Figure 4:
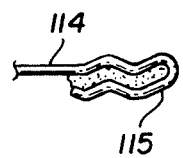
FIG. 4 illustrates a step in the method of making the device of FIG. 1.
Figure 9:
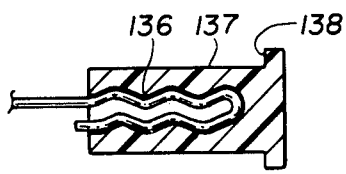
FIG. 9 illustrates the invention when used with an insert.

FIG. 9 illustrates an embodiment similar to that of FIG. 1 except that the elongated member is removably secured in an opening 136 of an insert 137. The insert 137 is adapted to be molded into the plate 101 and otherwise serves the same function as the opening 116 shown in FIG. 1. The insert 137 preferably has wings or other portions 138 so as to enhance engagement of the insert in the molded plate 101. The insert may be manufactured using the same molding technique as described above with respect to FIG. 4.

Figure 10:
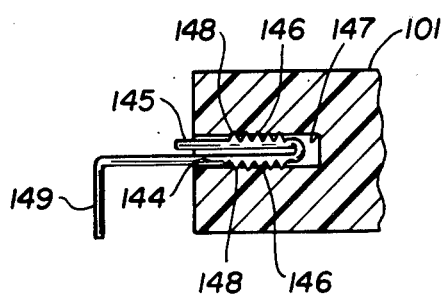
FIG. 10 illustrates a further modification of the invention.

FIG. 10 illustrates an embodiment wherein the elongated member 144 has a bent back portion 145, the bent back portion 145 and the end of the elongated portion 144 being serrated at, for example, 146. The inner surface of the opening 147 has depressions 148 generally corresponding to the serrations 140 so that when the elongated member 144 is pushed into the hole 147 the bent back member 145 is resiliently moved toward the main portion 144 and the serrations 146 engage the depressions 148 under the resilient force exerted by the bent back member 145. As described above with respect to FIGS. 1 and 2, the opening 147 may take a form similar to that of FIG. 2 to prevent rotation of the elongated member 144 therein. The elongated member 144 has a clasp 149 extending therefrom for engagement with a tooth or a tooth engaging auxiliary.

Figure 11:
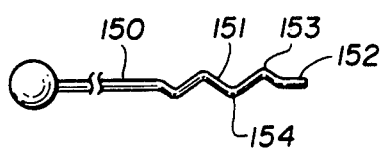
FIG. 11 illustrates a further embodiment of the invention.

FIG. 11 illustrates an embodiment of the invention which does not utilize a bent back portion. In the embodiment of FIG. 11, the elongated member 150 has an undulated or zig-zag end portion 151 which is adapted to be inserted into an opening, for example opening 116 in FIG. 1, of a plate member 101, or the like. The portion 151 of the elongated member 150 is resilient so that upon insertion into an opening which is suitably dimensioned to receive same, and which has suitable depressions such as depressions 117 in FIG. 1, the portion 151 flexes during insertion so as to provide positive engagement between the peaks of the undulations and the depressions of the opening of the plate member. Preferably the undulations are in a single plane and the opening in the plate member has a cross-sectional configuration similar to that of opening 116 in FIG. 2, but being suitably dimensioned to receive the elongated member 150. This prevents the elongated member 150 from rotating within the opening of the plate member. The end portion 152 of the elongated member is preferably straight or is otherwise shaped and directed relative to the last peak 153 so as to facilitate insertion of the elongated member 150 in the opening of a plate member.

When inserting the elongated member 150 of FIG. 11 into a suitably dimensioned opening, such as opening 116 of FIG. 1, the opposing peaks 153, 154, for example, of the elongated member will be resiliently moved toward each other until the respective peaks 153, 154, etc. engage the respective depressions 117 in the opening 116. Thus, by virtue of the peaks being resiliently deflected toward each other, the elongated member will be slightly resiliently deformed in its longitudinal direction during insertion and removal of the elongated member from the opening.

As should be apparent, various modifications and alterations can be made to the present inventive concept within the spirit and scope of the invention as set forth in the appended claims. For example, the plate 101 can be made from various materials, such as rigid plastics, as mentioned above, and the elongated members are preferably made of wire which has spring characteristics to provide proper resiliency of the bent back portion with respect to the remainder of the elongated member. The various illustrated elongated members can be modified with respect to their surface configurations for engagement in corresponding or mating surface configurations on the interior surface of the whole in which the elongated members are to be inserted. Other modifications and alterations will be apparent to those skilled in the art.

I claim:

1. A method of making an orthodontic appliance comprising:

forming an elongated member with a main portion and a bent back portion thereon, said main and bent back portions being spaced from each other;

forming undulations on a surface of at least one of said main and bent back portions;

filling said space between said main and bent back portions with a filler material which is later removable;

molding a member around said main and bent back portions with said filler material therebetween so that said molded member may have an inner surface substantially conforming to the outer surface configuration of said main and bent back portions; and then removing said filler material from the space between said main and bent back portions to permit said main and bent back portions to be resiliently deformed toward each other.

2. A method according to claim 1, comprising filling said space with a wax filler material.

3. A method according to claim 2, wherein said step of removing said filler material comprises applying heat to said filler material.

4. A method according to claim 1, wherein said step of removing said filler material comprises applying heat to said filler material.

* * * * *